US00PP32534P3

(12) United States Plant Patent
Castellarin et al.

(10) Patent No.: US PP32,534 P3
(45) Date of Patent: Dec. 1, 2020

(54) GRAPEVINE PLANT NAMED 'KERSUS'

(50) Latin Name: ***Vitis vinifera* L.**
Varietal Denomination: KERSUS

(71) Applicants: UNIVERSITÀ DEGLI STUDI DI UDINE, Udine (IT); ISTITUTO DI GENOMICA APPLICATA, Udine (IT)

(72) Inventors: Simone Diego Castellarin, Vancouver (CA); Guido Cipriani, Faedis (IT); Gabriele Di Gaspero, Cividale del Friuli (IT); Michele Morgante, Tricesimo (IT); Enrico Peterlunger, Codroipo (IT); Raffaele Testolin, Udine (IT)

(73) Assignees: UNIVERSITÀ DEGLI STUDI DI UDINE, Udine (IT); ISTITUTO DI GENOMICA APPLICATA, Udine (IT)

( * ) Notice: Subject to any disclaimer, the term of this patent is extended or adjusted under 35 U.S.C. 154(b) by 0 days.

(21) Appl. No.: 16/602,639

(22) Filed: Nov. 12, 2019

(65) Prior Publication Data

US 2020/0205332 P1 Jun. 25, 2020

(30) Foreign Application Priority Data

Dec. 20, 2018 (QZ) ..... PBR 20183519

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./205, 207
See application file for complete search history.

*Primary Examiner* — Susan McCormick Ewoldt
(74) *Attorney, Agent, or Firm* — Klarquist Sparkman, LLP

(57) ABSTRACT

A new grape variety distinguished by its high vigour, circular shaped leaves, medium weight fruit clusters, early-medium harvesting time (end of August in northeastern Italy), green dorsal and ventral internodes, and resistance to downy mildew and powdery mildew.

4 Drawing Sheets

Latin name of the genus and species of the plant claimed: *Vitis vinifera* L.
Variety denomination: 'KERSUS'.

CROSS REFERENCE TO RELATED APPLICATIONS

This application claims the benefit of priority from QZ Community Plant Variety Office (CPVO) Application No. 20183519, filed Dec. 20, 2018.

BACKGROUND

The present application relates to a new and distinct variety of grape named 'KERSUS'. Our new plant resulted from a controlled cross and is a selection from crossing SK-00-1/7 (unpatented) as the seed parent with Pinot Blanc (unpatented) as the pollen parent in 2005. The resulting plant was selected in 2013 when growing in a cultivated area in Udine, Italy.

'KERSUS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production.

SUMMARY

The 'KERSUS' variety is distinguished from other grape varieties due to the following unique combination of characteristics: high vigour, circular shaped leaves, medium weight fruit clusters, early-medium harvesting time (end of August in northeastern Italy), green dorsal and ventral internodes, and resistance to downy mildew and powdery mildew. A comparison of the new variety to its parents, *Vitis vinifera* 'Pinot blanc' (unpatented) and *Vitis* cross 'SK-00-1/7' (unpatented), and to the variety 'PINOT ISKRA' (co-pending application Ser. No. 16/602,637) is provided in Table 1.

TABLE 1

| Characteristic | 'Kersus' | 'PINOT ISKRA' |
|---|---|---|
| vigour | High | Medium-high |
| growth habit | Semi-erect | Semi-erect |
| leaf | Medium, dark green color (upper surface) RHS N134A, very few hairs in both surfaces, circular shape, small teeth | Very small to small, dark green color (upper surface) RHS N134A, very few hairs in both surfaces, pentagonal shape, medium teeth, strong blistering of upper side of blade |

TABLE 1-continued

| | | |
|---|---|---|
| cluster | low weight, cylindrical with one or two middle size wings, compact, globose berry, berry skin with yellow-green color RHS 150C, soft flesh, neutral taste, no flesh coloration | low weight, cylindrical with one or two middle size wings, compact, globose berry, berry skin with yellow-green color, soft flesh, neutral taste, no flesh coloration |
| harvesting time | Early-medium [End of August (Middle Friuli, northeastern Italy)] | Early-medium [end of August (Middle Friuli, northeastern Italy)] |
| resistances | Resistant to downy mildew, resistant to powdery mildew. | Resistant to downy mildew and to powdery mildew |
| internode color | Dorsal: green Ventral: green RHS 140B | Dorsal: red and green Ventral: red RHS 53A and green RHS 140B |

| Characteristic | Female Parent 'SK-00-1/7' | Male Parent Pinot blanc |
|---|---|---|
| vigour | Medium | Medium |
| growth habit | Semi-erect | Semi-erect |
| leaf | Medium, pentagonal shape, medium teeth, medium blistering of upper side of blade | Medium, dark green color (upper surface) RHS N134A, very few hairs in both surfaces, pentagonal shape, small teeth |
| cluster | medium weight, cylindrical, globose berry, berry skin with yellow-green color, soft flesh, neutral taste, no flesh coloration | low weight, with one or two wings, compact, broad ellipsoid berry, berry skin with yellow-green color RHS 154C, soft flesh, neutral taste, no flesh coloration |
| harvesting time | Medium [early September (Middle Friuli, northeastern Italy)] | Medium [early September (Middle Friuli, northeastern Italy)] |
| resistances | Resistant to downy mildew, resistant to powdery mildew. | No resistance to downy mildew, no resistance to powdery mildew |
| internode color | Dorsal: green Ventral: green 140B | Dorsal: green and red Ventral: green RHS 140B and red RHS 53A |

Of the many commercial cultivars known to the present inventor, the most similar to the new grapevine 'KERSUS' is the male parent 'Pinot blanc', to which a comparison has been provided above.

Asexual reproduction of this new variety by grafting onto K5BB rootstock was first performed in February 2014 in Rauscedo, Friuli Venezia Giulia Region, Italy, and has demonstrated that the foregoing characteristics for the new cultivar come true to form, are firmly fixed, and are established and transmitted through succeeding propagations. The new cultivar reproduces true to type.

Certain characteristics of this variety may change with changing environmental conditions (such as photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to The Royal Horticultural Society (R.H.S.) Colour Chart, 5th edition, London, England, 2007.

Figure 1:
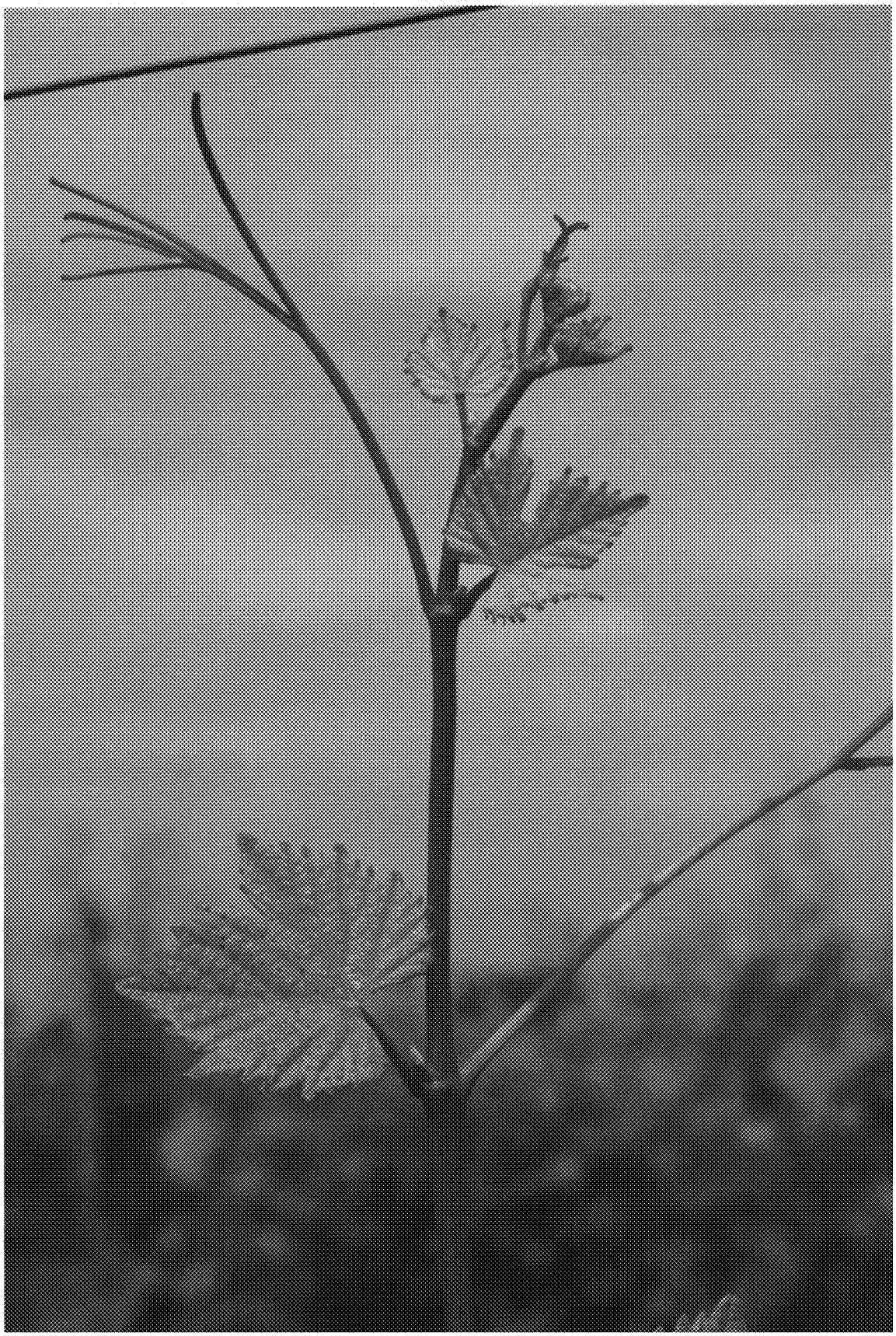
FIG. 1 is a photograph showing a shoot a leaf of the new variety 'Kersus' taken on May 24, 2017, in Rauscedo, Italy.
Figure 2:
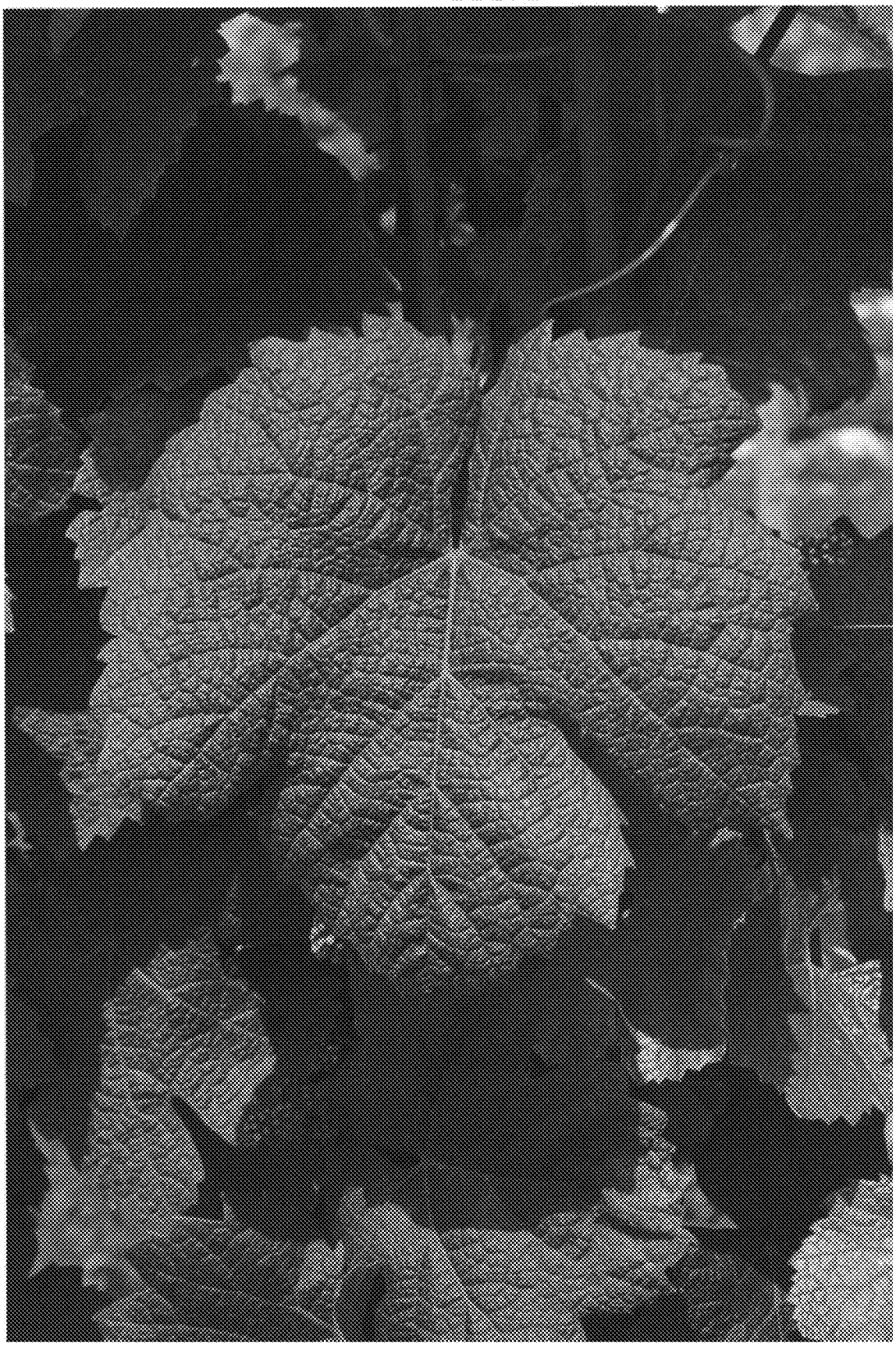
FIG. 2 is a photograph showing a leaf of the new variety 'Kersus' taken on May 24, 2017, in Rauscedo, Italy.
Figure 3:
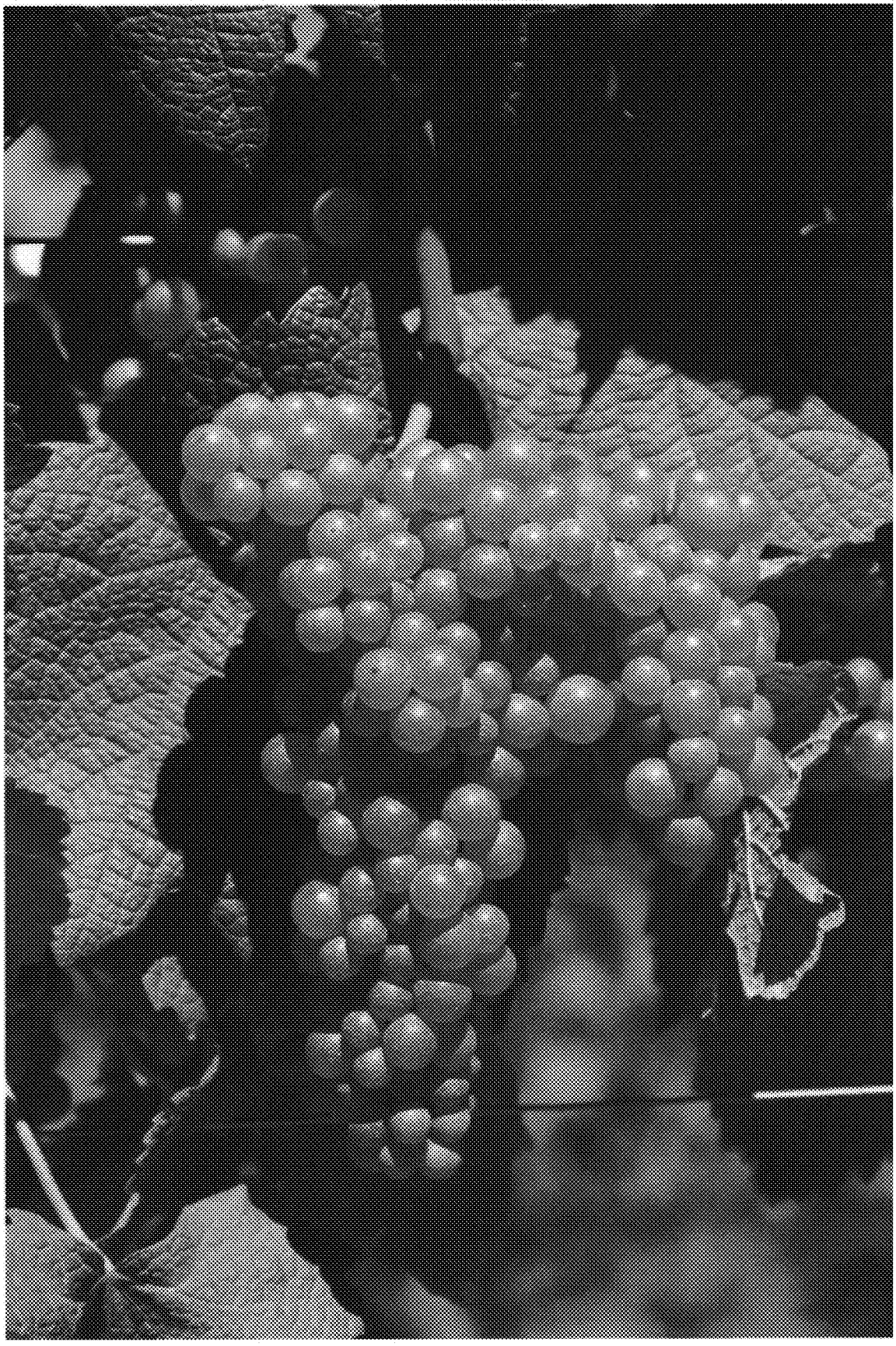
FIG. 3 is a photograph showing fruit of the new variety 'Kersus' taken on Aug. 24, 2016, in Rauscedo, Italy.
Figure 4:
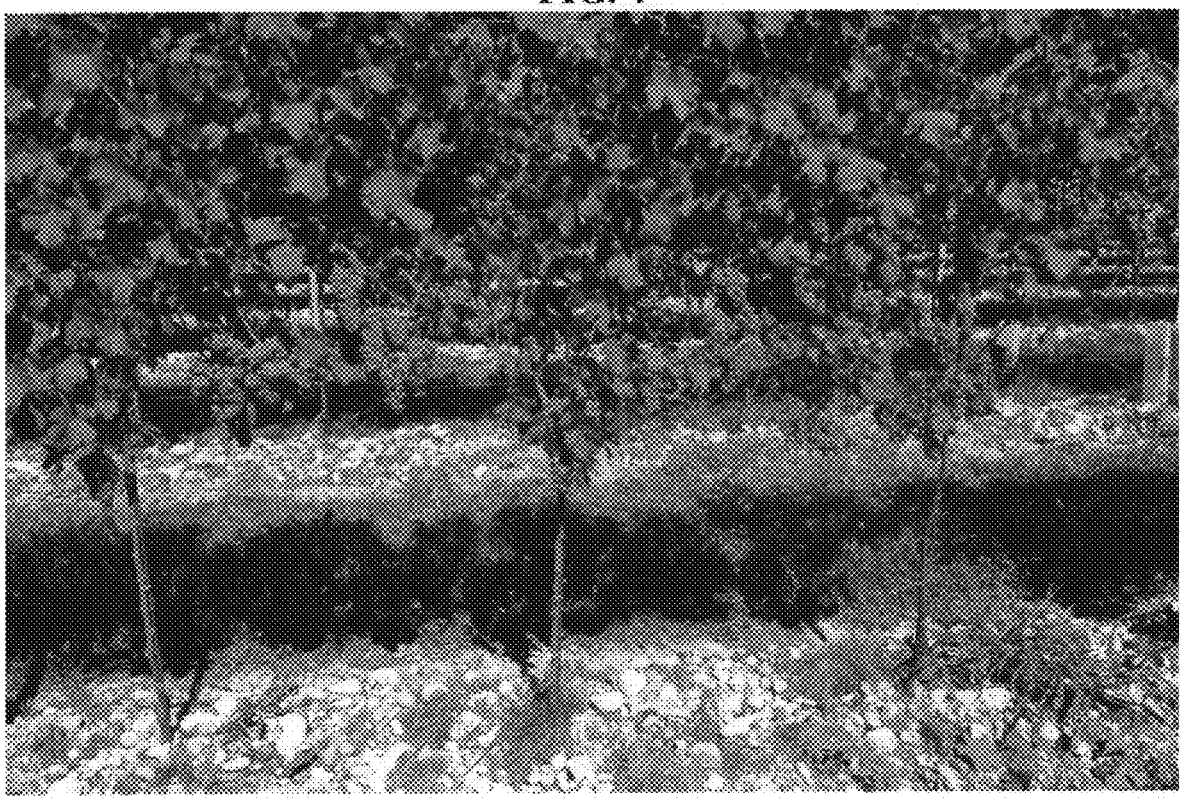
FIG. 4 is a photograph showing a plant of the new variety 'Kersus' taken on Aug. 24, 2016, in Rauscedo, Italy.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

Botanical

The following detailed description of the 'KERSUS' variety is based on observations of asexually reproduced progeny. The observed progeny are plants which were 3-5 years of age. The following detailed description concerns the plants growing in an open field taken in Rauscedo, Italy in 2016-2018. The original plant and progeny have been observed growing in a cultivated area in Rauscedo, Italy, with medium texture soil that is rich in skeleton and alluvial in nature. Temperatures in Rauscedo, Italy range from a high of 29° C. to a low of −2° C. Average rainfall is 822 mm per year, with an average rainfall during the growing season (April-September) of 453 mm. The chart used in the identification of colors described herein is The R.H.S. Colour Chart, $5^{th}$ edition, except where general color terms of ordinary significance are used. The color values were determined in August-September 2018 under natural light conditions in Rauscedo, Italy.

Scientific name: *Vitis vinifera* L.

Parentage:

*Seed parent*.—Sk-00-1/7.

*Pollen parent*.—Pinot Blanc.

Plant:

*Vigor*.—High.

*Growth habit*.—Semi-erect.

Trunk:
*Diameter at 50 cm.*—3.1 cm (6 yr-old plants).
*Bark texture.*—Striate.
*Bark coloration.*—RHS 187A.

Mature cane:
*Diameter.*—9.6 mm.
*Bark texture.*—Ribbed.
*Bark coloration.*—RHS 179C.

Shoot:
*Opening of the shoot tip.*—Fully open for young shoot.
*Distribution of the anthocyanin coloration of the prostrate hairs of the shoot tip.*—Absent.
*Density of prostate hair on the shoot tip.*—Medium-to-high.
*Attitude (before tying).*—Semi-erect.
*Color of the dorsal side of internodes.*—Green 140B.
*Color of the ventral side of internodes.*—Green 140B.
*Distribution of anthocyanin coloration on the bud scales.*—Absent.
*Number of consecutive tendrils.*—2 or less.

Tendrils:
*Length.*—21.9 cm.
*Diameter.*—2.4 mm.
*Color.*—RHS 150A.

Leaves:
*Shape.*—Circular.
*Ratio length/width of teeth.*—Small (Marsanne), both sides convex.
*Arrangement of lobes of upper lateral sinuses.*—Absence of sinus (Melon).
*Blistering.*—Medium-to-strong blistering of upper side of mature blade.
*Size of blade.*—Medium (Cabernet Sauvignon); average length 121 mm; average width 181 mm.
*Young leaf.*—Color of upper surface is green RHS 134B, color of the lower surface RHS 142C, with sparse prostrate hairs between main veins on the lower side of blade.
*Mature leaf.*—Color of upper surface is dark green RHS N134A, color of the lower surface RHS 140B, with sparse prostrate hairs between main veins on the lower side of blade.
*Mature leaf.*—Three lobes.
*Area of anthocyanin coloration of main veins on upper side and lower of mature blade.*—Absent.
*Area of anthocyanin coloration of main veins on lower side of mature blade.*—Absent.
*Goffering/depressions of mature blade between the main veins.*—Absent or very weak (Gamay).
*Profile of mature leaf in cross section.*—V-shaped.
*Degree of mature leaf opening of petiole sinus.*—Closed.
*Shape of base of petiole sinus.*—Brace-shaped ({)-to-V-shaped.
*Petiole sinus base limited by vein.*—Not limited.
*Petiole length compared to length of middle vein.*—Equal (Garnacha tinta).
*Petiole average length.*—117.5 mm.
*Petiole color (upper surface).*—RHS 145B and RHS 184D.
*Petiole color (lower surface).*—RHS 145B and RHS 184D.
*Density of prostrate hairs on petiole.*—None or very low.
*Density of erect hairs on petiole.*—None or very low.
*Depth of upper lateral sinuses.*—Absent or very shallow; average depth of the sinus 35.2 mm.

Flower bud:
*Shape.*—Round.
*Size.*—Average.
*Color.*—Light brown.
*Bud burst.*—Beginning of April in Rauscedo, Italy.

Flowers: Fully developed stamens and fully developed gynoecium.
*Insertion of 1st inflorescence.*—3rd and 4th node.
*Number of inflorescences per shoot.*—1 to 2.
*Flowering period (time of beginning of flowering).*—Beginning of June in Rauscedo, Italy.
*Average flower diameter.*—2 mm.
*Inflorescence average length.*—155 mm.
*Inflorescence average width.*—121 mm.

Fruit:
*Cluster.*—Low weight (about 260 g), cylindrical with one or two middle size wings, compact.
*Time of beginning of berry ripening.*—Early.
*Berry shape.*—Globose.
*Berry length.*—Short (about 13 mm).
*Berry width.*—Narrow (about 13 mm).
*Berry bloom.*—Medium.
*Thickness of berry skin.*—Medium-to-thick.
*Color of skin (without bloom).*—Yellow green 150C.
*Texture.*—Soft flesh.
*Flesh color.*—RHS 150C.
*Anthocyanin coloration of flesh.*—Absent or very weak.
*Flavor.*—None/neutral.
*Berry shipping quality.*—N.a.
*Berry storage quality.*—N.a.
*Formation of seeds.*—Complete.
*Average number of seeds.*—2-3.
*Seed size.*—Medium (Pinot noir, Merlot).
*Seed color.*—Brown RHS 200C.
*Harvest time.*—Early-medium (end of August in north-eastern Italy).
*Bunch length (peduncle excluded).*—Medium (about 160 mm; Syrah).
*Bunch width.*—Narrow (about 80 mm; Riesling, Sauvignon).
*Bunch density.*—Dense.
*Length of peduncle of primary bunch.*—Very short-to-short (up to about 30 mm; Silvaner).
*Color of peduncle.*—RHS 156A and RHS N200A.
*Diameter of peduncle.*—4-5 mm.
*Lignification of peduncle.*—Up to about the middle.
*Berry hilium.*—Visible.

Pedicel:
*Average length.*—9-12 mm.
*Average diameter.*—1-1.5 mm.
*Color.*—RHS 145B.

Grape juice characteristics:
*Sugars (brix).*—21.1.
*PH.*—3.4.
*Total acidity.*—6.2 g/l.
*Tartaric acid.*—6.57 g/l.
*Malic acid.*—1.89 g/l.

Production characteristics:
*Clusters per shoot.*—1.42.
*Grape production.*—3467 g/plant.
*No. of bunches/vine (at harvest).*—15.2.
*Average weight of the bunch.*—262.7 g.
*Average berry weight.*—1.57 g.
*Pruning wood weight.*—690 g/plant.
*Index of ravaz.*—5.02.

Wine produced from grapes:
*Total acidity.*—5.3 g/l.
*Tartaric acid.*—2.5 g/l.
*PH.*—3.37.

*Net extract.*—20.0 g/l.
*Alcohol.*—12.8 g/l.
*Volatile acidity.*—0.2 g/l.
*Reducing sugars.*—1.1 g/l.

TABLE 2

| Molecular Analysis | | | | | |
|---|---|---|---|---|---|
| VVS2 | | VVMD5 | | VVMD7 | |
| N + 10 | N + 14 | N + 10 | N + 16 | N + 12 | N + 26 |
| VVMD25 | | VVMD27 | | VVMD28 | |
| N + 6 | N + 14 | N + 10 | N + 14 | N + 20 | N + 28 |
| VVMD32 | | VRZAG62 | | VRZAG79 | |
| N + 5 | N + 5 | N + 14 | N + 20 | N + 2 | N + 24 |

Use international coding based on "N" (see European project GENRES 081—A basis for the preservation and utilization of *Vitis* genetic resources)

Phenological characteristics (in Rauscedo, Italy):

*Germination*.—April 4.
*Flowering*.—June 2.
*Veraison* (*change of color*).—August 7.
*Maturation*.—September 9.

Use: Wine grape.

Disease/pest resistance: Resistance to downy mildew and powdery mildew.

We claim:

1. A new and distinct variety of *Vitis vinifera* L. plant substantially as illustrated and described herein.

* * * * *